United States Patent [19]
Hawn et al.

[11] Patent Number: 5,743,737
[45] Date of Patent: Apr. 28, 1998

[54] DENTAL INSTRUMENT

[75] Inventors: Kirk G. Hawn, P.O. Box 337, Lovettsville, Va. 22080; James T. Lindsay, Lovettsville, Va.

[73] Assignee: Kirk G. Hawn, Lovettsville, Va.

[21] Appl. No.: 596,867

[22] Filed: Feb. 9, 1996

[51] Int. Cl.$^6$ .......................................... A61C 3/00
[52] U.S. Cl. .................... 433/141; 433/147; 81/177.8
[58] Field of Search .......................... 433/141, 146, 433/147; 81/57.5, 177.8, 177.85, 438, 439, 440, 489

[56] References Cited

U.S. PATENT DOCUMENTS

| | | | |
|---|---|---|---|
| D. 260,355 | 8/1981 | Buzzell. | |
| 550,508 | 11/1895 | How. | |
| 736,101 | 8/1903 | Hough | 433/147 |
| 797,270 | 8/1905 | Dreher. | |
| 1,356,372 | 10/1920 | Kelly. | |
| 1,420,279 | 6/1922 | Parsons et al. | 81/177.8 |
| 1,616,300 | 2/1927 | Bido. | |
| 2,690,617 | 10/1954 | Giern et al. | 433/147 |
| 2,806,706 | 9/1957 | Fitch. | |
| 2,817,258 | 12/1957 | Stein. | |
| 3,471,929 | 10/1969 | Boone | 433/147 |
| 4,056,020 | 11/1977 | Couiello | 81/177.85 |
| 4,323,347 | 4/1982 | Weissman | 433/141 |
| 4,399,723 | 8/1983 | Marleau | 81/439 |
| 4,436,005 | 3/1984 | Hanson. | |
| 4,461,192 | 7/1984 | Suligoy et al. | |
| 4,552,531 | 11/1985 | Martin. | |
| 4,631,770 | 12/1986 | Goldberg. | |
| 4,780,923 | 11/1988 | Schultheiss | 433/147 |
| 4,893,529 | 1/1990 | Lin. | |
| 4,899,415 | 2/1990 | Wheeler | 81/438 |
| 5,028,234 | 7/1991 | Schweitzer et al. | 433/147 |
| 5,179,748 | 1/1993 | Lipic. | |
| 5,329,834 | 7/1994 | Wong. | |
| 5,480,166 | 1/1996 | Milsop | 81/437 |

FOREIGN PATENT DOCUMENTS

| | | | |
|---|---|---|---|
| 3412475 | 10/1985 | Germany | 433/147 |
| 615339 | 1/1980 | Switzerland | 433/141 |
| 2278280 | 11/1994 | United Kingdom | 433/141 |

OTHER PUBLICATIONS

Pfingst & Company, Inc., 1983 Catalog No. 33 South Plainfield, N.J. 07080, p. 91.

Dentsply Order Form, Dentsply, Inc., 15821 Ventura Blvd., Suite 420, Encino, CA 91436.

Dentsply Technical Bulletin, "Surgical Procedures for Bio-Vent Implants", etc., Dentsply, Inc., 15821 Ventura Blvd., Suite 420, Encino, CA 91436.

Dentsply, Inc. 1992 Brochure, pp. 5–6, Swede–Vent™, Instruments & Equipment, Dentsply, Inc., 15821 Ventura Blvd., Suite 420, Encino, CA 91436. © 1992.

Dentsply, Inc. 1992 Brochure, pp. 1–2, Spectra–System™, Abutments, Dentsply, Inc., 15821 Ventura Blvd., Suite 420, Encino, CA 91436. © 1992.

Dentsply, Inc., page from Catalog entitled, "Spectra–System™ Packaging", Dentsply, Inc., 15821 Ventura Blvd., Suite 420, Encino, CA 91436.

Dentsply, Inc., page from Catalog entitled "Swede–Vent System Packaging", Dentsply, Inc., 15821 Ventura Blvd., Suite 420, Encino, CA 91436.

Dentsply Technical Bulletin, "One Standardized Hex Tool For All TS Series Abutments", Dentsply, Inc., 15821 Ventura Blvd., Suite 420, Encino, CA 91436.

(List continued on next page.)

*Primary Examiner*—Ralph Lewis
*Attorney, Agent, or Firm*—Banner & Witcoff, Ltd.

[57] ABSTRACT

A dental instrument for performing a variety of procedures includes an elongate, rigid body and a bit. The body preferably includes an axial bore and at least one lateral bore. The axial bore holds the bit so that it extends outward along the longitudinal axis of the body. The lateral bore holds the bit so that it projects laterally outward at an acute angle to the longitudinal axis.

29 Claims, 11 Drawing Sheets

OTHER PUBLICATIONS

Catalog page, "Instruments, Operative", Sullivan Dental Products, Inc., 10920 W. Lincoln Ave., West Allis, WI 53227.

Catalog page, The Supply House, 11291 Sun Rise Park Drive, Rancho Cordova, CA 95742.

Catalog, pp. 281–282, "Procedural Supplies & Equipment—Periodontics", Ace Surgical Supply Co., 1034 Pearl Street, P.O. Box 1710, Brockton, MA 02403.

Catalog, p. 215, "Instruments", Henry Shine, 5 Harbor Park Dr., Fort Washington, NY 11050.

Catalog, p. 158, "Crown Removers", BENCO, 11 Bear Creek Blvd., Wilkes–Barre, PA 18702.

Catalog, p. 67, "Instruments–Operative", Sullivan.

Catalog, p. 280, "Procedural Supplies & Equipment—Periodontics", Ace Surgial Supply Co., 1034 Pearl Street, P.O. Box 1710, Brockton, MA 02403.

DENTAL INSTRUMENT

FIELD OF THE INVENTION

The present invention pertains to a hand manipulable instrument used to perform dental procedures.

BACKGROUND OF THE INVENTION

Dentists have long relied upon many different implements to perform dental work (e.g., crown removal, root sectioning, etc.). Typically, dental implements are specially designed and configured to perform only a single procedure. As a result, the dentist must keep and maintain a large assortment of instruments. In addition to the large number of required instruments, a number of the instruments have either lacked the desired strength or been too expensive to manufacture. The need exists, therefore, for a dental instrument which has considerable strength, is inexpensive to manufacture, and is capable of use in a wide range of procedures.

SUMMARY OF THE INVENTION

A dental instrument in accordance with the present invention includes an elongate, rigid body and a bit projecting from the body. In the preferred construction, the body includes an axial bore and at least one lateral bore for alternatively supporting a bit. The axial bore holds the bit so that it extends outward along the longitudinal axis of the body. The lateral bore holds the bit so that it projects laterally from either side from the body. In this way, the bit can be mounted in either bore depending on the procedure to be performed and the location of the affected tooth. Moreover, different bits can also be secured within the bores as needed. The versatility provided by the bores and the plurality of bits enables the instrument to be used for a number of separate and distinct procedures.

The dental instrument of the present invention also has a sturdy construction which provides substantial strength for any of the desired procedures. In the preferred embodiment, the elongate body has a solid, unitary construction. The thickness (or diameter) of the body is selected to provide a high level of strength and yet be easily manipulated by a dentist. The bores defined in the body are formed to provide solid support for each of the bits against a wide array of forces which may be applied. Further, as can be appreciated, the formation of bores to secure the bits in the solid body enables the present invention to be manufactured inexpensively.

The bits can be advantageously mounted to the body in order to ease the operation of the present dental instrument. More specifically, the bits can be mounted to project laterally from the body at an acute or obtuse angle to the body's longitudinal axis. With this construction, the body can be angled toward or away from the remote working end of the bit to thereby maximize the instrument's effectiveness for each procedure.

Similarly, bits which have a remote working end defined as a blade edge can be secured such that the blade edge lies in a plane that is inclined relative to the longitudinal axis of the body in two orthogonal directions. The body is then not only angled toward or away from the working end, but is also angled upward or downward relative to the engaged tooth. Accordingly, the dentist is given freedom to orient the body in the most advantageous position for the particular procedure to be performed.

DETAILED DESCRIPTION OF THE PREFERRED EMBODIMENTS

A dental instrument 10 in accordance with the present invention comprises a body 12 and a bit 14 (FIGS. 1, 2, 7a and 7b). The body is adapted to act as a handle, pry bar, and/or lever for performing various dental procedures. Bit 14 is provided to project outward from the body to engage the desired tooth or dental article.

Body 12 is an elongate, rigid member formed with a forward section 16, a middle section 17, and a rear section 18 (FIGS. 1, 2, 7a and 7b). The body is preferably composed of stainless steel; nevertheless, other materials which are suitable for dental work and which provide the requisite strength could also be used. In the preferred embodiment, body 12 is a solid, cylindrical member having a diameter sized to provide considerable strength and yet be easily manipulated by a dentist. One preferred embodiment includes a body having a length of about five inches and a diameter of about 0.375 inch.

Figure 1:
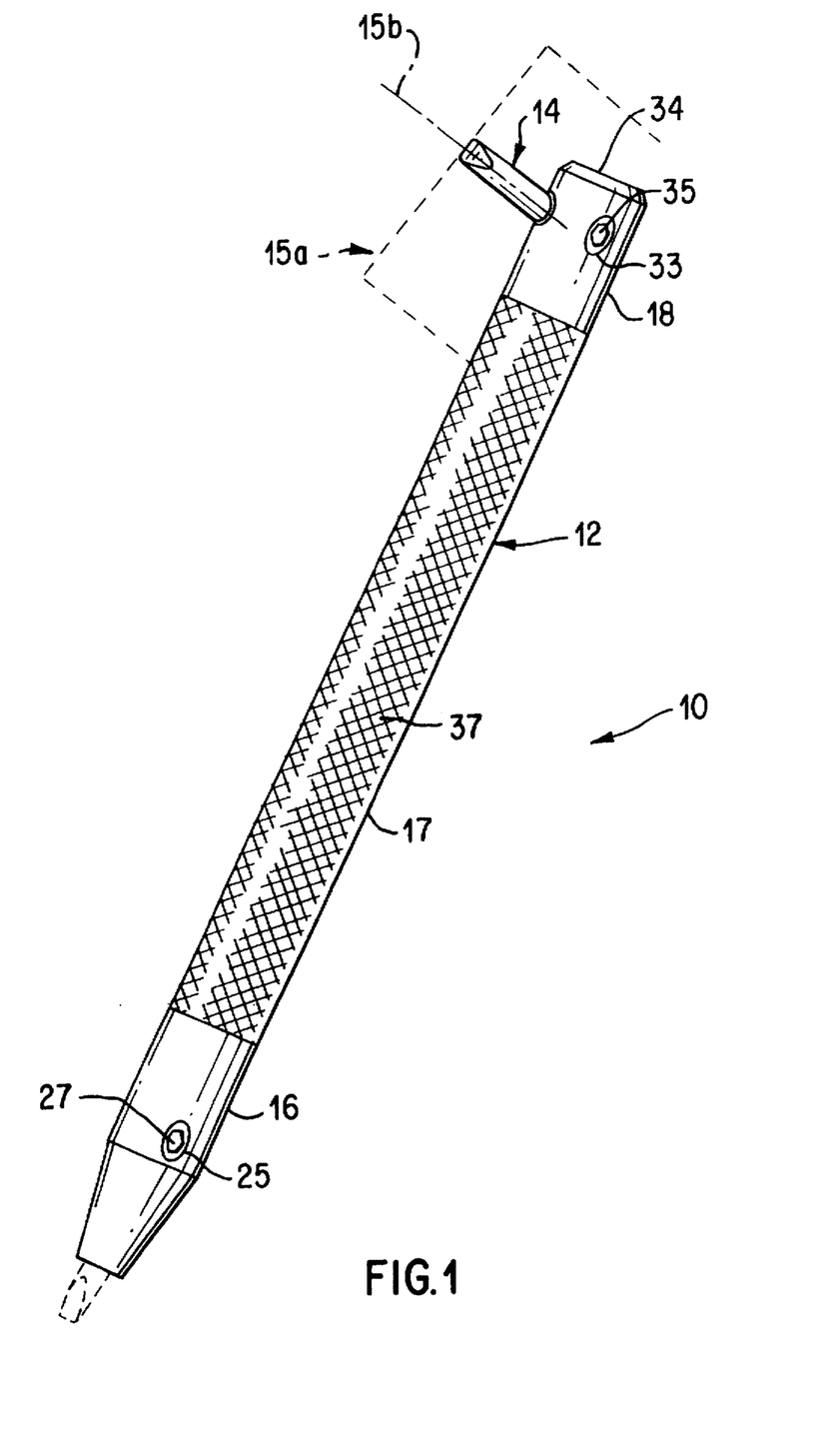
FIG. 1 is a perspective view of a dental instrument in accordance with the present invention.
Figure 2:
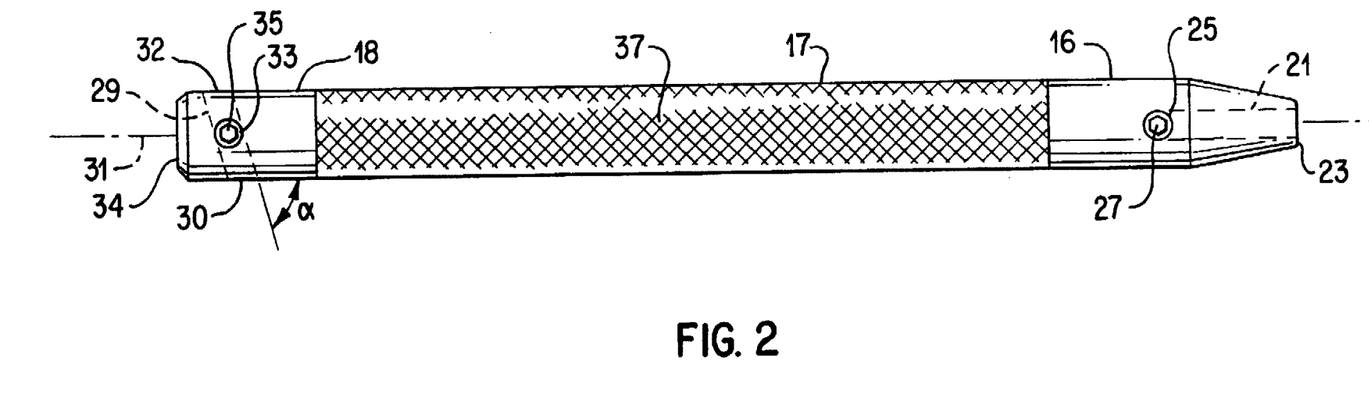
FIG. 2 is a side view of a body of the dental instrument.

The forward section 16 of the body includes an axial bore 21 which is adapted to receive a bit 14 (FIGS. 1 and 2). Axial bore 21 opens in the front end 23 of body 12 so that the bit projects axially forward from the body. A threaded hole 25 is also defined in forward section 16 such that it intersects axial bore 21. A set screw 27 is threaded into hole 25 to secure bit 14 in axial bore 21. In this arrangement, bit 14 can be installed or removed by simply tightening or loosening set screw 27. Nevertheless, other arrangements for securing the bit in bore 21 could be used.

Figures 7A, 7B:
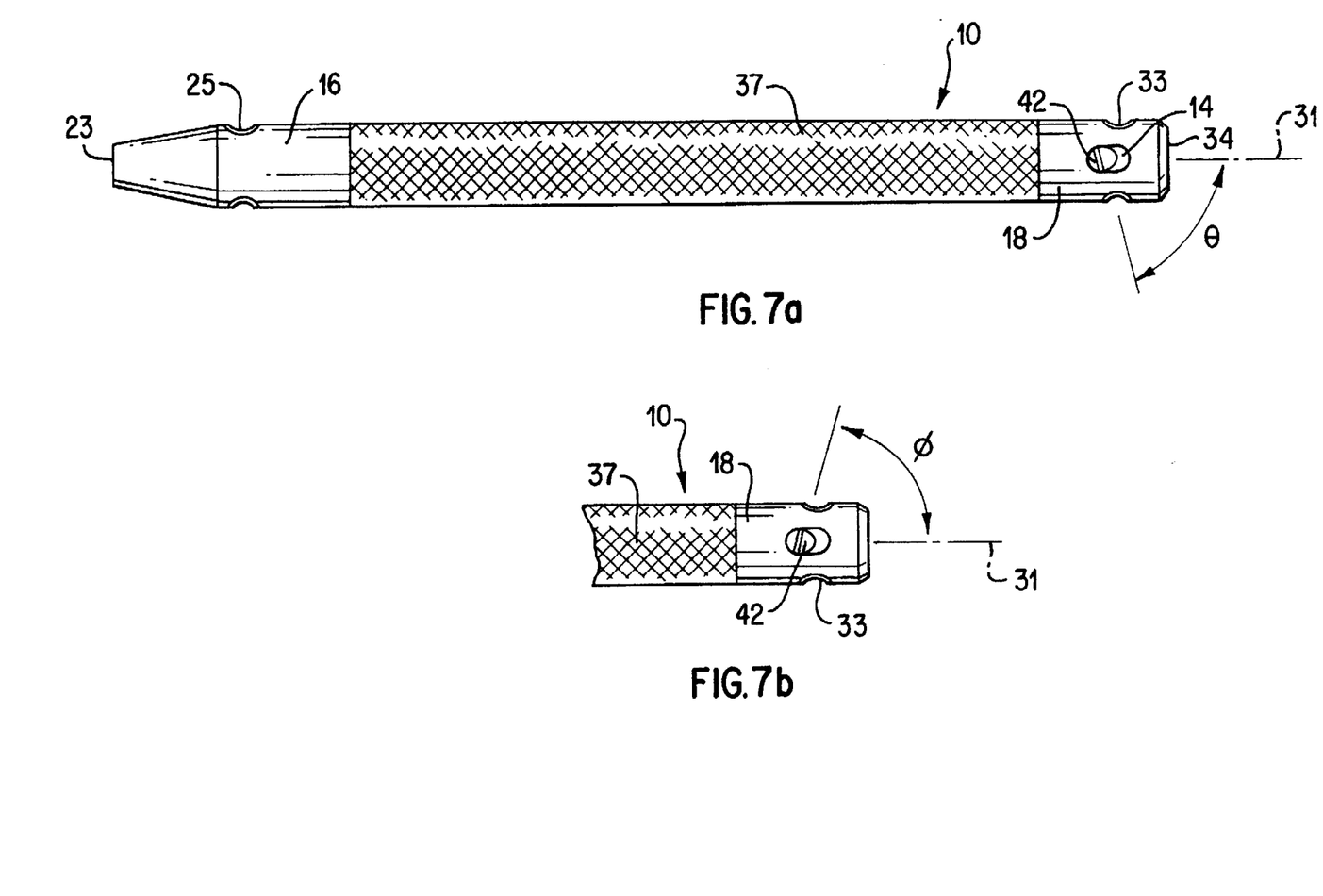
FIG. 7a is a side view of the dental instrument with a bit secured in a bore.
FIG. 7b is a partial side view of the dental instrument with the bit secured in an alternative position in the bore.

Rear section 18 defines a lateral bore 29 which is also adapted to receive bit 14 (FIGS. 1, 2, 7a and 7b). Lateral bore 21 has a first end 30 and a second end 32 on opposite sides of body 12. The lateral bore is further formed at an acute angle α to longitudinal axis 31 of instrument 10 so that the bit projects laterally outward at an inclined orientation to body 12 (FIG. 2). Although the angle is discussed in terms of an acute angle, the angle could also be considered obtuse if measured in the opposite direction. In the preferred embodiment, lateral bore 29 extends through body 12 at an angle α of about 80°. The bit can be placed in bore 29 to project from either end 30 or 32 of bore 29 (FIG. 1, 2, 7a and 7b). When bit 14 projects from end 30, the working end is inclined in a direction toward front end 23 of instrument body 12 (FIGS. 7a and 7b). When bit 14 projects from end 32, the working end is inclined in a direction toward rear end 34 of instrument body 12 (FIG. 1). These orientations enable the dentist to position the body in the most advantageous position for the desired procedure.

Rear section 18 further includes a transverse threaded hole 33 which preferably is perpendicular to both lateral bore 29 and longitudinal axis 31 (FIGS. 1, 2, 7a and 7b). As with hole 25, a set screw 35 is threaded into hole 33 to secure bit 14 in the lateral bore. Instrument bit 14 can be installed and removed from lateral bore 29 by simply tightening or loosening set screw 35. Nonetheless, other arrangements for securing the bit into lateral bore 29 could be used.

Figure 1A:
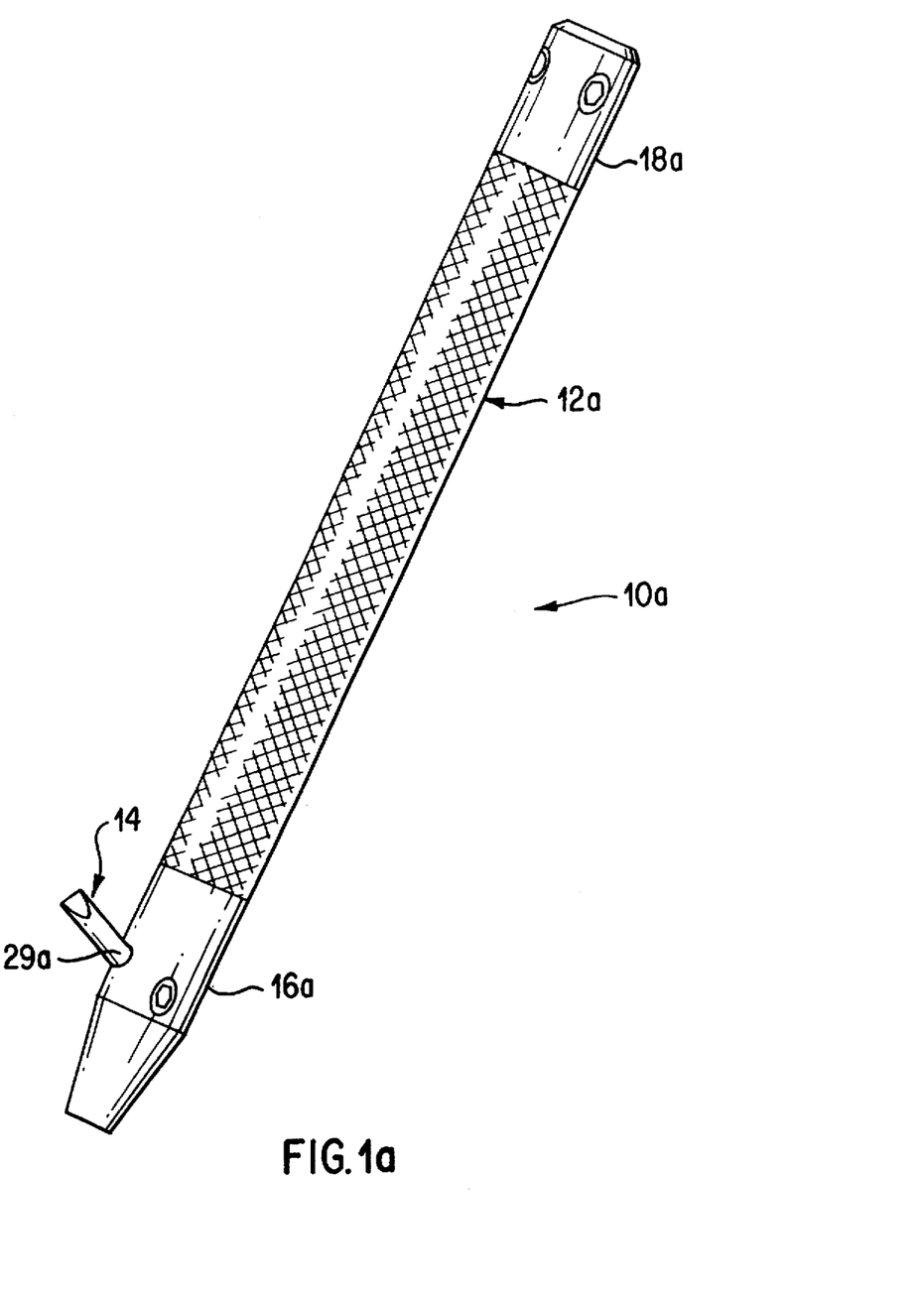
FIG. 1a is a perspective view of an alternative dental instrument in accordance with the present invention.
Figure 2A:
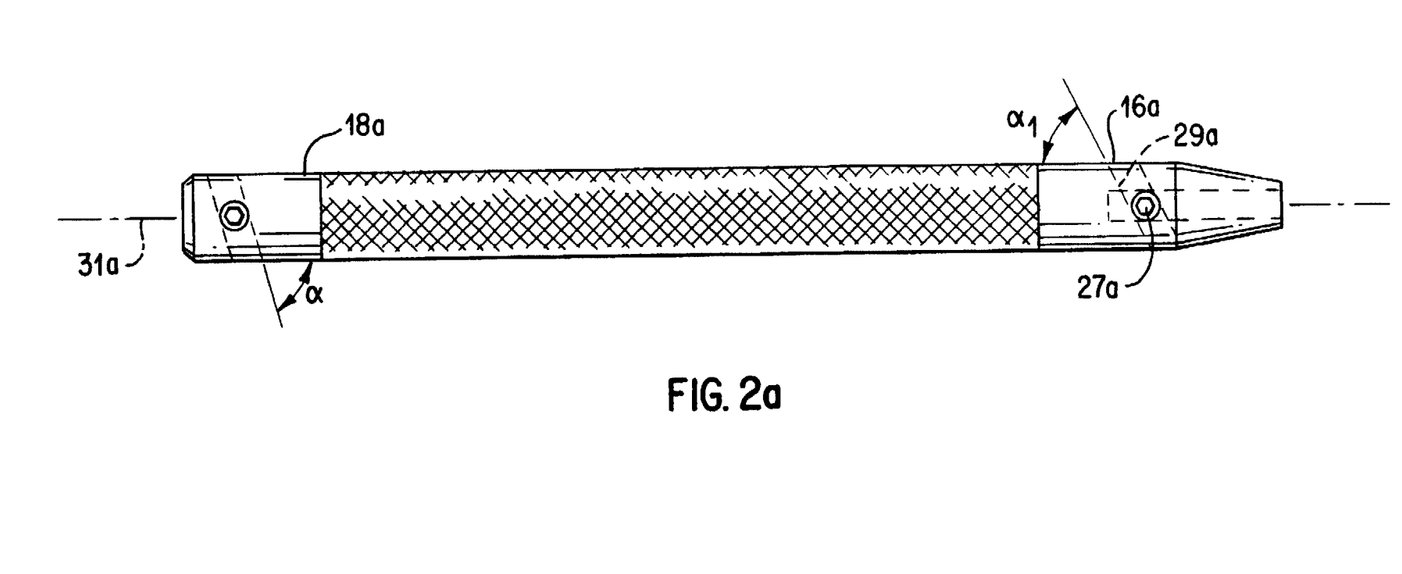
FIG. 2a is a side view of a body of the alternative dental instrument.

In an alternative embodiment, dental instrument 10a is essentially the same as instrument 10 except that it additionally includes a lateral bore 29a extending entirely through forward section 16a in addition to lateral bore 29' and axial bore 21' (FIGS. 1a and 2a). Bore 29a is formed at an acute angle $\alpha_1$ of preferably about 70° to axis 31a of instrument 10a so that the bit projects laterally outward at an inclination to body 12a. As discussed above with respect to bore 29, angle $\alpha_1$ is described as an acute angle but could be equally described as an obtuse angle if measured in the opposite direction. Bit 14 can be placed in bore 29a to project from either side of the instrument and secured by set screw 27a (i.e., the same screw which secures the bit in axial bore 21'). In use, bit 14 received in bore 29a would function in the same way as when received in bore 29. While bore 29a provides the dentist with additional options for mounting the bit, it also causes a reduction in the strength of the instrument. As another alternative, bore 29a could be formed in rear section 18a in lieu of bore 29.

Middle section has a knurled exterior 37 to avoid slippage and to ease handling by the dentist (FIGS. 1, 1a, 2, 2a, 7a, 7b). Instrument body 12 is preferably cylindrical to provide significant strength and ease of manufacturing. Moreover, the uniform cylindrical body enables the instrument to be easily held and manipulated in different orientations and for different procedures. The instrument body can be formed with a non-cylindrical shape, so long as the body is not unduly narrowed to cause significant lessening of its strength and/or economy of manufacture, or configured to hinder any of the desired operations.

Figure 3A:
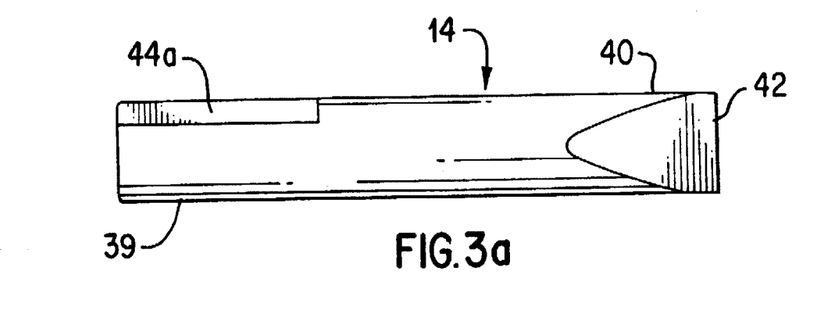
FIG. 3a is a top view of a bit for either dental instrument.
Figure 3B:
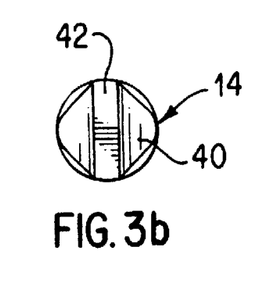
FIG. 3b is a front end view of the bit.
Figures 3C, 3D, 4A, 4B:
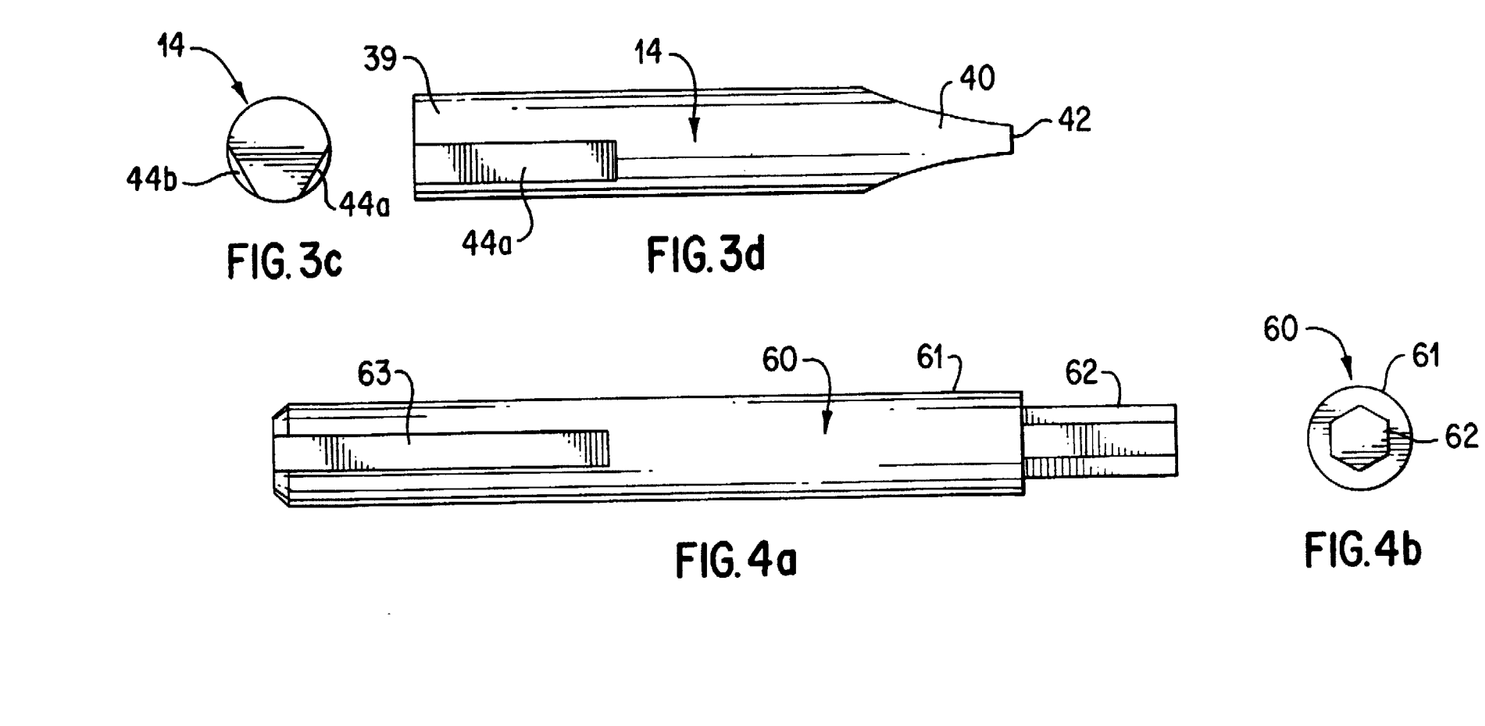
FIG. 3c is a rear end view of the bit.
FIG. 3d is a side view of the bit.
FIG. 4a is a side view of a second alternative bit.
FIG. 4b is front end view of the second alternative bit.
Figure 3E:
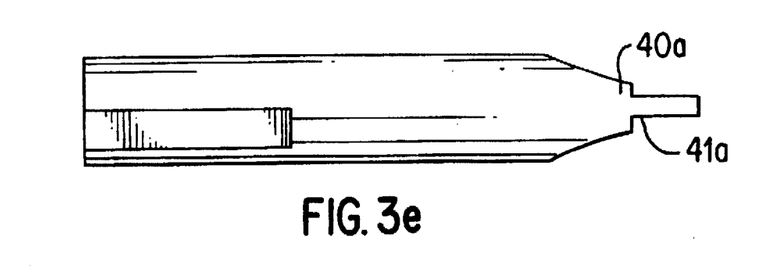
FIG. 3e is a side view of an alternative bit.

Different bits can be mounted into bores 21, 29, 29a to suit the particular procedure to be performed by the dentist. Bit 14 (FIGS. 3a–3d) includes a mounting end 39 to be received into one of the bores 21, 29, 29a and a remote working end 40 for engaging a tooth or dental article. Bit 14 is preferably formed as a generally linear rod member having primarily a cylindrical configuration. Working end 40 is provided with a flattened blade edge 42 which is adapted for prying or screwing. Alternatively working end 40a of bit 14a can be formed with a cut-out portion 41a (FIG. 3e). Although a bit of only one size is shown, bits of different lengths could be mounted in the bores 21, 29, 29a as needed. In any event, the bits are preferably composed of hardened stainless steel.

The bit mounting end 39 is generally cylindrical in shape and sized for mating receipt in either bore 21, 29, or 29a. Flats 44a, 44b are preferably provided to define a flat surface against which a set screw 27, 35 can firmly bear. The flats 44a, 44b are positioned on the bit in order to place blade edge 42 at an acute angle θ or φ to longitudinal axis 31 when bit 14 is mounted in lateral bore 29 or 29a (FIGS. 7a and 7b). As discussed above, the term acute angle could equally be replaced with the term obtuse angle when measured from the other direction. Flats 44a, 44b preferably lie in planes inclined to one another at an angle of about 30° to place blade edge 42 at an angle θ or φ of about 75° relative to axis 31. This locates blade edge 42 in a first plane 15a extending perpendicular to the longitudinal axis of bit 14, such that a second plane 15b extending along the length of blade edge 42 and perpendicular to first plane 15a bisects the longitudinal axis of bit 14. Nevertheless, other angular orientations could also be used as desired. Flats 44a, 44b are engaged by set screw 35 to set the desired position blade edge 42. This particular positioning of the flats enables instrument body 12 to be oriented either upward or downward with respect to the row of teeth or side of the face positioned by the affected tooth. As can be appreciated, this left/right, upward/downward orientation of body 12 provides the dentist with a greater freedom of motion in prying or screwing operations. The use of a plurality of flats on the bit make no difference when the bit is mounted in axial bore 21 because the bit extends axially from the body.

Figure 8:
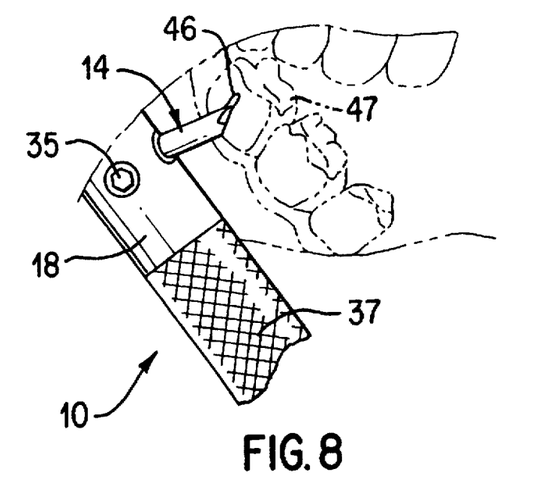
FIG. 8 is a perspective view of using the dental instrument to remove a crown from a posterior tooth.

As an example, instrument 10 can be used for removing a temporary or permanent crown 47 (FIG. 8). Instrument bit 14 can be mounted in lateral bore 29 (or 29a) for removal of crown 47 from a posterior tooth. In this particular instance, tool bit 14 is shown to be mounted to project from end 30 of lateral bore 29. Nevertheless, if desired by the dentist, the tool bit could be mounted to project from end 32 of bore 29. In any event, blade edge 42 is fit within slot 46 cut into the crown 47. Body 12 is then rocked up and down to pry the crown from the cement layer which attaches it to the tooth. As can be appreciated, the solid body forms a lever which permits the dentist to apply substantial prying pressures to the crown. Moreover, the orientation of the body up and away from the tooth—caused by the inclined position of blade edge 42—provides a wide range of prying action for the dentist in both directions.

Figure 9:
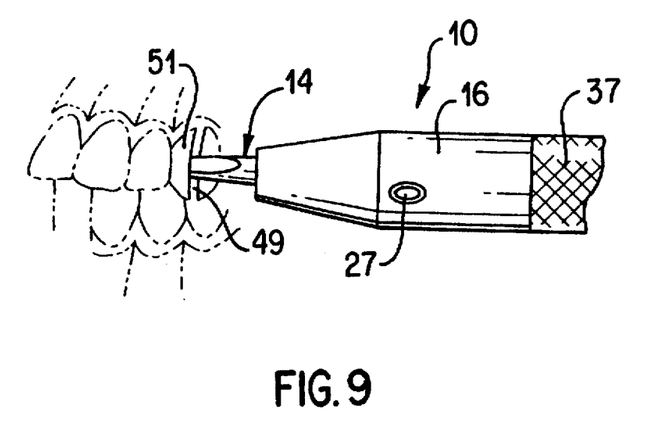
FIG. 9 is a perspective view of using the dental instrument to remove a crown from an anterior tooth.

As another example, instrument 10 can also be used to remove a crown 51 from an anterior tooth (FIG. 9). With the tooth positioned near the front of the mouth, the dentist may desire to place bit 14 in axial bore 21. Similar to the removal of a crown from a posterior tooth, blade edge 42 is fit within a slot 49 cut within crown 51. The tool is then turned and/or rocked to pry crown 51 from the cement layer which attaches the crown to the tooth.

Figure 10:
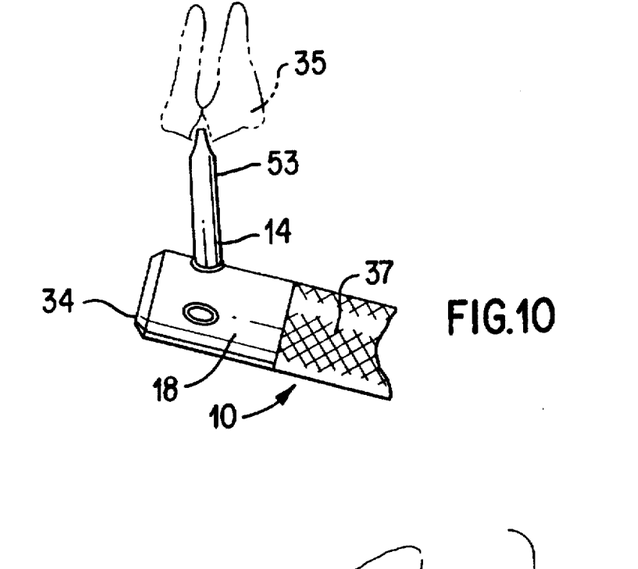
FIG. 10 is a side view of using the dental instrument for root sectioning.

As another example, instrument 10 can be used in a root sectioning procedure (FIG. 10). According to this example, a slot 53 can be cut into tooth 55 from above. The blade edge 42 of bit 14 mounted in lateral bore 29 (or 29a) is placed into the slot, and rocked back and forth until the tooth is cracked down through the roots. Again, the sturdy construction of the instrument permits sufficient pressure to be applied by the dentist to accomplish the necessary tasks.

Figure 4C:
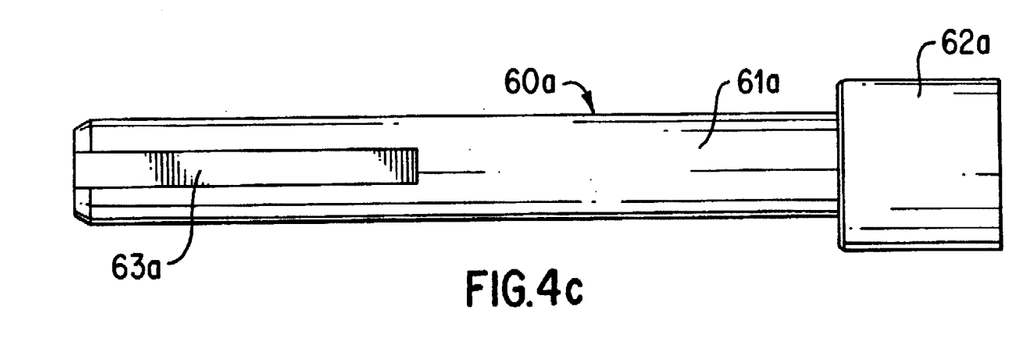
FIG. 4c is a side view of a third alternative bit.
Figure 4D:
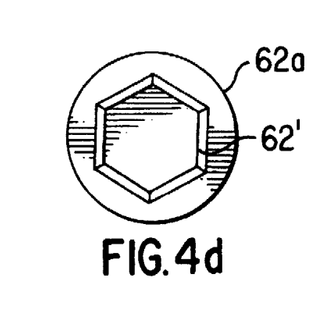
FIG. 4d is a front view of the third alternative bit.
Figure 4E:
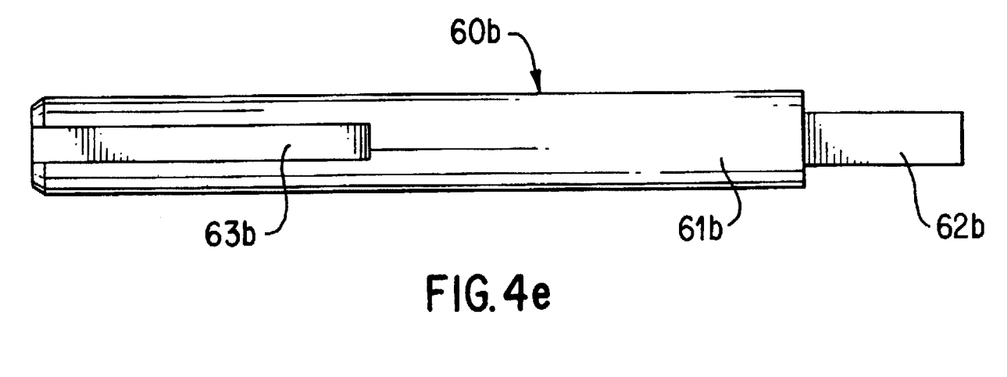
FIG. 4e is a side view of a fourth alternative bit.
Figure 4F:
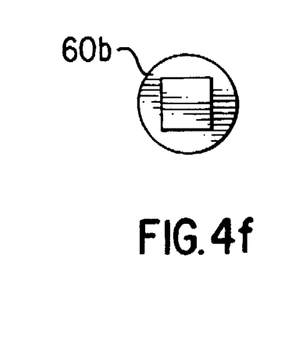
FIG. 4f is a front view of the fourth alternative bit.
Figure 11A:
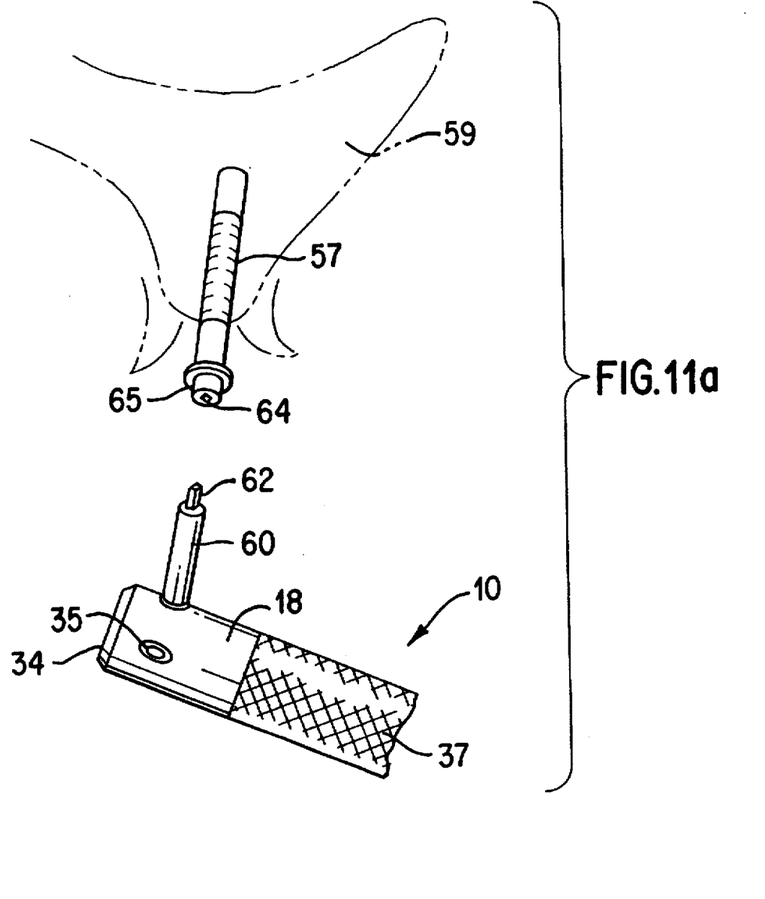
FIG. 11a is a side view of using the dental instrument with the second alternative bit for implant fixation.
Figure 11B:
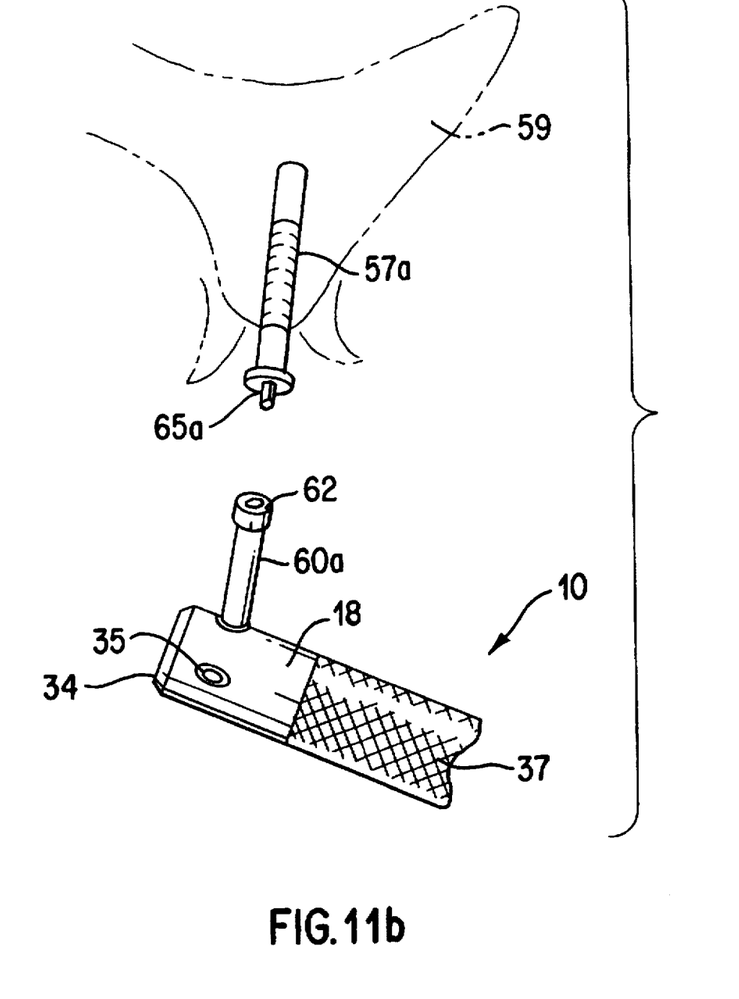
FIG. 11b is a side view of using the dental instrument with the third alternative bit for implant fixation.

As another alternative, bits 60, 60a, 60b (FIGS. 4a, 4b, 4c, 4d, 4e and 4f) can also be used for securing implants. Bit 60 preferably includes a generally cylindrical main portion 61 and a hex head 62 (FIGS. 4a and 4b) for receipt within a hex shaped recess 64 formed on the head 65 of the threaded post 57 (FIG. 11a). Bit 60a includes main portion 61a and head 62a which includes a hex recess 62' (FIGS. 4c and 4d) for receiving a hex shaped head 65a of a threaded post 57a of an implant (FIG. 11b). Similarly, bit 60b (FIGS. 4e and 4f) includes main portion 61b and head 62b which is square shaped for receipt into a square shaped recess of an implant. Bits 60, 60a, 60b further include a flat 63, 63a, 63b to be engaged by set screw 27 or 35. Bits adapted to fix implants into the jaw are preferably composed of titanium. Further the head of the bit could be shaped to match any structure (e.g., a differently shaped recess) formed on the head of the post.

Figures 5, 6A, 6B:
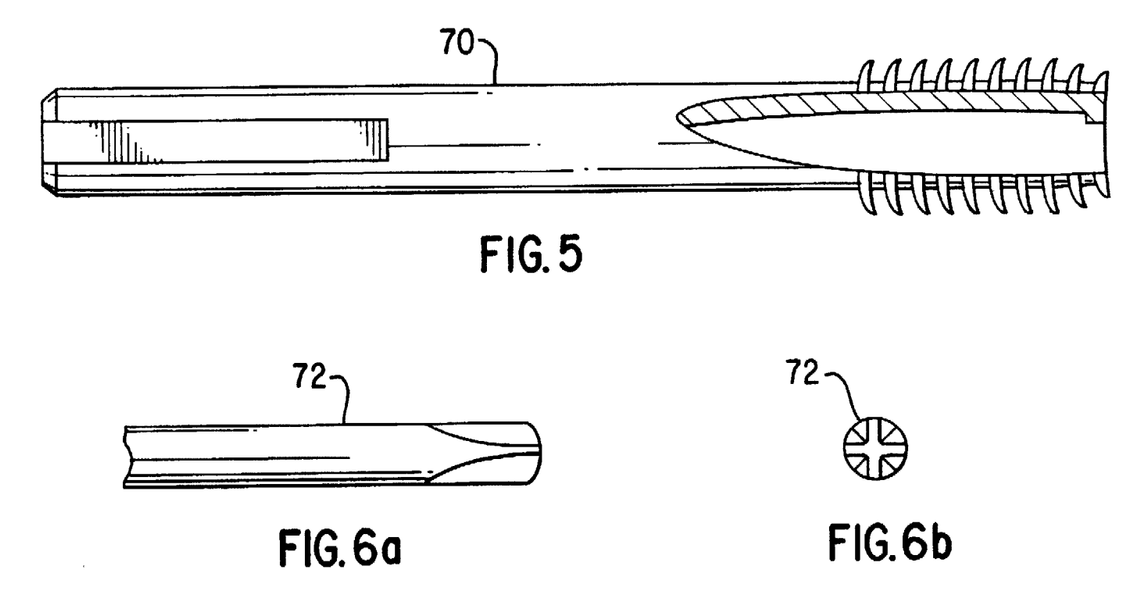
FIG. 5 is a side view of a fifth alternative bit.
FIG. 6a is a side view of a sixth alternative bit.
FIG. 6b is a front view of the sixth alternative bit.
Figure 6C:
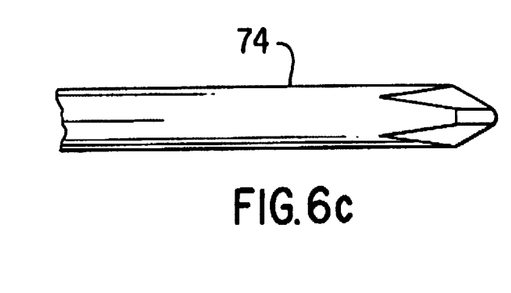
FIG. 6c is a side view of a seventh alternative bit.
Figure 6D:
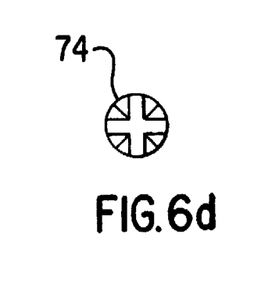
FIG. 6d is a front view of a seventh alternative bit.

FIGS. 11a and 11b illustrate the use of instrument 10 in implant fixation procedures. In this procedure, for example, a post 57, 57a is secured into a jaw 59 for the attachment of a replacement tooth member (not shown). According to this procedure, the hex head 62, 62a (or 62b) of bit 60, 60a (60b) can be used to engage a hex shaped recess 64 of head 65 or hex shaped head 65a to screw the post of the implant into the jaw 59. For the insertion of an implant in dense bone, a bit 70 formed as a bone tap (FIG. 5) can be mounted in bore 21, 29, 29a to thread the hole into which the implant is secured.

Finally, bits 72, 74 provided with a cross head or Phillips type end (FIGS. 6a, 6b, 6c and 6d) can be mounted in bores 21, 29, 29a for the fastening of screws in certain operations, such as rigid osseous screw fixation.

The above-discussion concerns the preferred embodiment of the present invention. Various other embodiments as well as many changes and alterations may be made without departing from the spirit and broader aspects of the invention as defined in the claims.

We claim:

1. A dental instrument comprising:
   an elongate, generally linear, rigid body having a, longitudinal axis and first and second ends, said body also having a first lateral bore extending in said body at an acute angle to said longitudinal axis and proximate said first end, a second lateral bore extending in said body at an acute angle to said longitudinal axis and proximate said second end, and an axial bore extending inwardly from one of said ends generally along said longitudinal axis;
   a bit having a mounting end secured within one of said bores and a working end opposite said mounting end, said bit projecting laterally from said body when said mounting end is sectored in one of said lateral bores; and
   a securing element for engaging said mounting end to hold said bit in one of said bores.

2. A dental instrument in accordance with claim 1, wherein said first lateral bore extends entirely through said body so as to define a first opening and a second opening, and wherein said instrument has the capacity to secure said bit to project from either said first opening or said second opening.

3. A dental instrument in accordance with claim 2, wherein said working end of said bit includes a flattened blade edge.

4. A dental instrument in accordance with claim 3, in which said blade edge extends in a plane which is inclined at acute angles to said longitudinal axis of said instrument in different orthogonal directions.

5. A dental instrument in accordance with claim 4, wherein said mounting end of said bit includes at least one flat, and said securing element is capable of engaging said flat to hold said bit in one of said bores.

6. A dental instrument in accordance with claim 5, in which said mounting end includes a pair of flats which extend in planes that are inclined at an angle of about thirty degrees relative to each other.

7. A dental instrument in accordance with claim 5, wherein said securing element is a set screw received in a threaded hole in said body.

8. A dental instrument in accordance with claim 2, wherein said mounting end of said bit includes at least one flat, and said securing element is capable of engaging said flat to hold said bit in one of said bores.

9. A dental instrument in accordance with claim 1, in which said second lateral bore extends at an angle of about 70° relative to said longitudinal axis.

10. A dental instrument in accordance with claim 1, wherein said working end of said bit includes a flattened blade edge.

11. A dental instrument in accordance with claim 10, wherein said bit is generally linear and has a bit axis extending therethrough, and wherein said blade edge extends in a plane which generally coincides with the bit axis to form a first acute angle relative to said longitudinal axis of said instrument in one direction and to form a second acute angle to said longitudinal axis in another direction orthogonal to said one direction.

12. A dental instrument in accordance with claim 11, in which said first acute angle is about 80°.

13. A dental instrument in accordance with claim 12, in which said second acute angle is about 75°.

14. A dental instrument in accordance with claim 11, in which said first acute angle is about 70°.

15. A dental instrument in accordance with claim 11, in which said second acute angle is about 75°.

16. A dental instrument in accordance with claim 1, wherein said working end of said bit includes a hex shaped head.

17. A dental instrument in accordance with claim 1 in which said bit includes a head with a hex shaped recess.

18. A dental instrument in accordance with claim 1, wherein said mounting end of said bit includes at least one flat, and said securing element is capable of engaging said flat to hold said bit in one of said bores.

19. A dental instrument in accordance with claim 1, in which said body includes a knurled medial segment.

20. A dental instrument in accordance with claim 1, in which said acute angle defined between said first lateral bore and said longitudinal axis is about 80°.

21. A dental instrument in accordance with claim 1, in which said acute angle defined between said lateral bore and said longitudinal axis is about 70°.

22. A dental instrument in accordance with claim 1, in which said body includes at least an elongate section having a substantially uniform thickness.

23. The dental instrument in accordance with claim 1, wherein the magnitude of said acute angle at which said first lateral bore extends relative to said longitudinal axis of said body is different than the magnitude of said acute angle at which the second bore extends relative to said longitudinal axis of said body.

24. The dental instrument in accordance with claim 1, wherein said securing element engages a bit positioned in said first lateral bore, and further comprising a second securing element for engaging a second bit in said second lateral bore.

25. A dental instrument comprising:

an elongate rigid body having a longitudinal axis, said body including a bore extending therein at an acute angle; and a bit having a longitudinal axis and secured within said bore so as to project laterally from said body at an acute angle to the longitudinal axis of said body and terminating in an end surface for engaging a tooth or a dental article, said engaging end surface lies in a first plane that extends perpendicular to the longitudinal axis of said bit such that a second plane extending perpendicular to the first plane and along the length of said engaging end surface bisects the longitudinal axis of said bit and forms an acute angle with the longitudinal axis of the body.

26. A dental instrument in accordance with claim 25, in which said body includes a second lateral bore for receiving said bit.

27. A dental instrument in accordance with claim 26, in which said body further includes a pair of ends and an axial bore opening at one of said ends, wherein said axial bore is adapted to receive therein said bit.

28. A dental instrument in accordance with claim 26, wherein said bit includes a mounting end opposite said engaging end surface, said mounting end of said bit includes at least one flat, and said instrument further includes a securing element for engaging said flat to hold said bit in said lateral bore.

29. A dental instrument in accordance with claim 28, in which said mounting end of said bit includes a pair of flats, wherein said flats are inclined at an angle of about thirty degrees relative to each other.

* * * * *